(12) United States Patent
Mark et al.

(10) Patent No.: US 6,245,084 B1
(45) Date of Patent: Jun. 12, 2001

(54) SYSTEM FOR CONTROLLING A MOTOR DRIVEN SURGICAL CUTTING INSTRUMENT

(75) Inventors: Joseph L. Mark, Indianapolis; Michael E. Miller, Trafalgar; Miklos T. Kara, Indianapolis, all of IN (US); Daniel John Henry, Winchester, VA (US); Brian McCary, St. Louis, MO (US)

(73) Assignee: Promex, Inc., Franklin, IN (US)

( * ) Notice: Subject to any disclaimer, the term of this patent is extended or adjusted under 35 U.S.C. 154(b) by 0 days.

(21) Appl. No.: 09/175,293

(22) Filed: Oct. 20, 1998

(51) Int. Cl.[7] ............................................. A61B 17/32
(52) U.S. Cl. ................................... 606/167; 606/170
(58) Field of Search ................................ 606/167, 170, 606/171, 176, 180

(56) References Cited

U.S. PATENT DOCUMENTS

| Re. 34,556 | 3/1994 | Sjostrom et al. . |
|---|---|---|
| 4,167,943 | 9/1979 | Banko . |
| 4,200,106 | 4/1980 | Douvas et al. . |
| 4,203,444 | 5/1980 | Bonnell et al. . |
| 4,210,146 | 7/1980 | Banko . |
| 4,274,414 | 6/1981 | Johnson et al. . |
| 4,345,192 | 8/1982 | Kohzai et al. . |
| 4,403,179 | 9/1983 | Kohzai et al. . |
| 4,705,038 | 11/1987 | Sjostrom et al. . |
| 4,867,155 | 9/1989 | Issacson . |
| 4,995,877 | 2/1991 | Ams et al. . |
| 5,030,900 | 7/1991 | Kono et al. . |
| 5,048,538 | 9/1991 | Terwilliger et al. . |
| 5,059,204 | 10/1991 | Lawson et al. . |
| 5,171,245 | 12/1992 | Cezana . |
| 5,207,697 | 5/1993 | Carusillo et al. . |
| 5,222,953 | 6/1993 | Dowlatshahi . |
| 5,269,794 | 12/1993 | Rexroth . |
| 5,270,622 | 12/1993 | Krause . |
| 5,403,276 | 4/1995 | Schechter et al. . |
| 5,411,513 | 5/1995 | Ireland et al. . |
| 5,602,449 | 2/1997 | Krause et al. . |
| 5,669,921 | 9/1997 | Berman et al. . |
| 5,672,945 | 9/1997 | Krause . |
| 5,733,298 | 3/1998 | Berman et al. . |

FOREIGN PATENT DOCUMENTS

WO 95/03001    2/1995  (WO) .

Primary Examiner—Kevin Truong
(74) Attorney, Agent, or Firm—Baker & Daniels (57) ABSTRACT

A system is provided for controlling the stopping position of a surgical cutting tool relative to a tissue entrance location of a cannula housing the cutting tool. A signal processor is responsive to a motor activation signal to provide a motor activation signal to a motor control unit for driving a motor, which activates the cutting tool positioned in a cannula. The signal processor is responsive to a motor stop signal and to a stop position signal to stop the cutting tool relative to the tissue entrance location of the cannula to thereby avoid trapping a portion of the tissue base between the cutting tool and a boundary of the cannula opening.

20 Claims, 7 Drawing Sheets

SYSTEM FOR CONTROLLING A MOTOR DRIVEN SURGICAL CUTTING INSTRUMENT

FIELD OF THE INVENTION

The present invention relates generally to systems for controlling motor driven surgical cutting instruments, and more specifically to such systems for controlling the position of the surgical cutting instrument upon stoppage of the drive motor. More particularly, the invention relates to controlling a brush type DC motor used to drive the cutting instrument.

BACKGROUND OF THE INVENTION

Minimally invasive surgical cutting instruments are known and widely used to excise and remove biological tissue. Such instruments typically include a handpiece comprising a cutting tool housed within an elongated cannula, wherein the tool is disposed adjacent to an opening at or near the tip of the cannula. The cannula itself is configured for percutaneous insertion into a body via a small incision, and is manually maneuvered into position for tissue excision and removal.

Various configurations of cutting tools are known and may be driven manually, pneumatically or via an electrically controlled drive motor. In any case, tissue adjacent to the opening near the tip of the cannula is typically excised by driving the cutting tool with either a rotary or reciprocal motion relative to the cannula, whereby tissue is drawn into the opening (typically via vacuum) and excised by the cutting tool.

While motor driven surgical cutting instruments of the type just described have been widely used in surgical applications, many presently available designs suffer from a variety of drawbacks. For example, if the position of the cutting tool is not controlled when the drive motor is disabled, there exists a possibility that the cutting tool may come to rest in a position that traps or pinches unexcised tissue between a cutting surface of the cutting tool and the opening near the tip of the cannula. To avoid this problem, surgeons must typically maintain activation of the drive motor as the tip of the instrument is moved or removed from the surgical site, thereby compromising the accuracy and precision of the procedure. The foregoing drawback becomes more problematic as the complexity of the procedure increases, and is of particular concern when performing delicate procedures such as removing vitreous tissue during ocular surgery.

Designers of such surgical cutting instruments have attempted to address the foregoing problem by providing various systems for controlling motor position when stopping or disabling the drive motor. An example of one such system for controlling the position of a three-phase brushless DC motor is given in U.S. Pat. No. 5,602,449 to Krause, et al. The Krause et al. disclosure discloses an elaborate control system including multiple sensors for determining motor armature position at 6° intervals. As is known in the art, brushless DC motors are typically speed driven rather than torque driven and accordingly have little rotational resistance associated with the operation thereof. Controlled stoppage of such a motor is thus extremely difficult, if not impossible, when the motor is operating at a high rotational speed, and the Krause et al. system is accordingly responsive to a motor stop signal to first decrease motor speed below some threshold speed level and then perform a controlled stop based on armature position.

Brushed DC motors, as compared with brushless DC motors, are typically torque driven rather than speed driven, and accordingly have a substantial rotational resistance associated therewith. Thus, while the Krause et al. system may effectively provide for controlled stopping of a surgical cutting instrument driven by a brushless DC motor, such elaborate control techniques are unnecessary when driving a brushed DC motor. What is therefore needed is a simple and inexpensive control technique for controlling the stop position of a brushed DC motor driven surgical instrument. Ideally the control system should be operable to control the position of the cutting tool when the drive motor is turned off so that unexcised tissue is not trapped between the cutting tool and the opening near the tip of the cannula.

SUMMARY OF THE INVENTION

The foregoing shortcomings of the prior art are addressed by the present invention. In accordance with one aspect of the present invention, a tissue cutting apparatus comprises an elongated housing configured for insertion into a body site, the housing having a first end defining an opening adjacent thereto. A tissue cutting tool is disposed within the housing and defines at least one cutting surface configured for movement relative to the housing adjacent the opening to thereby excise tissue extending into the opening.

In one feature of the invention, a brushed DC motor drives a drive shaft coupled to the cutting tool. While the brushed motor is rotary, the cutting tool can be driven in a rotary or reciprocating fashion with an appropriate transmission mechanism between the drive shaft and cutting tool. Means are provided for sensing a predefined position of the drive shaft relative to the housing and producing a stop position signal corresponding thereto. In one embodiment, the sensing means is a Hall effect sensor and magnet arranged between the motor and the cutting tool.

A motor control circuit is provided to control operation of the motor. In one embodiment, the circuit includes a pulse-width-modulated controller. In another embodiment, the motor control circuit utilizes a current feedback to control the motor current. With either embodiment, the motor control circuit is operable in response to a motor stop signal to stop the motor with the drive shaft at the predefined position. Certain features of the motor control circuit are configured to take advantage of the natural braking characteristics of the motor and cutting tool in order to stop the motor at the appropriate position. This predefined position is arranged to orient the cutting surface of the cutting tool relative to the opening to avoid trapping unexcised tissue between the cutting surface and a boundary of the opening.

In one embodiment of the invention, the motor control circuit includes an op amp driven current feedback loop to control the current provided to the brushed motor. A switch is interposed in the feedback loop to disable the current feedback signal when it is desired to stop the motor. Eliminating the current feedback improves the braking characteristics of the motor and handpiece so that the cutting blade can be accurately stopped in its predetermined position. With this embodiment, the control circuit can respond to a motor stop signal to activate the feedback loop switch. The motor is powered until the stop position signal is received indicating that the drive shaft is at the predetermined position, at which point current to the motor is ceased to stop the cutter.

In another embodiment, the control circuit is responsive to a motor stop signal to drive the motor at a predefined motor speed less than the cutter operating speed. The control circuit is also responsive to a second occurrence of the stop position signal to deactivate the motor with the drive shaft at the predefined position.

One object of the present invention is to provide an improved surgical cutting apparatus that is operable to avoid trapping unexcised tissue between the cutting tool and a boundary of the opening in the cannula when the cutting tool drive motor is deactivated.

Another object of the present invention is to provide such improvements to surgical cutting apparatuses that have either a rotating cutting tool or a linearly reciprocating cutting tool.

These and other objects of the present invention will become more apparent from the following description of the preferred embodiment.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Figure 1:
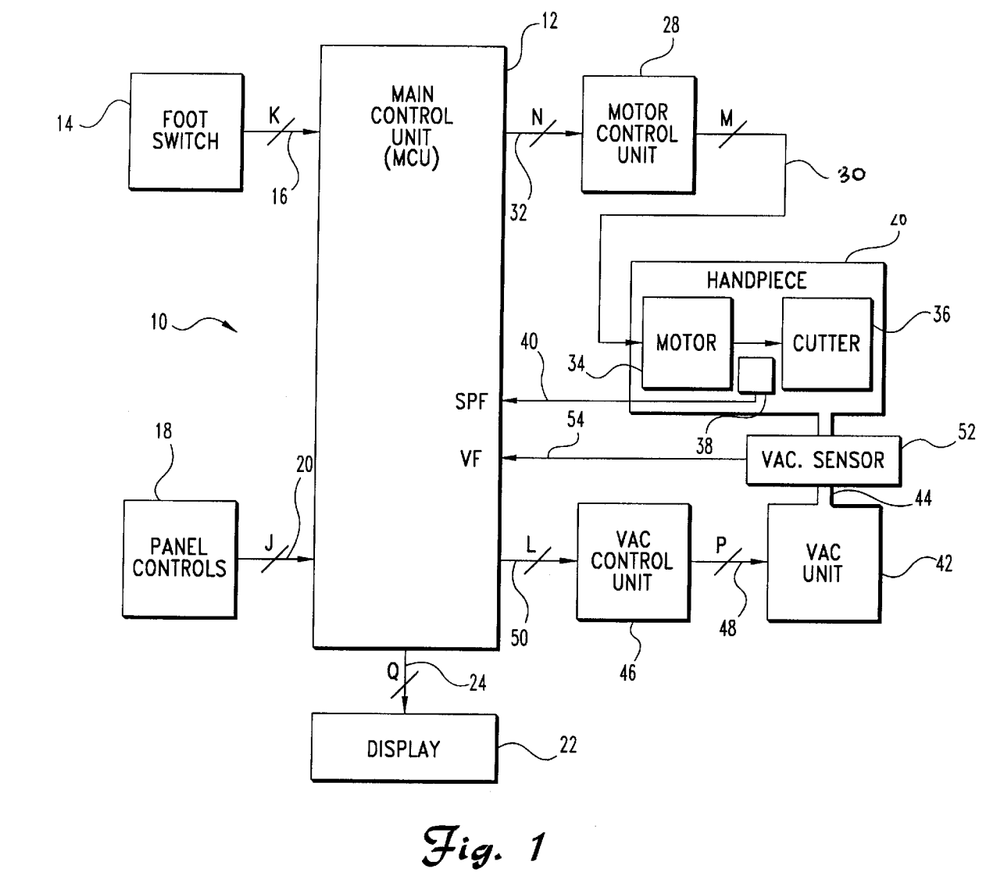
FIG. 1 is a diagrammatic illustration of one embodiment of a system for controlling the brushed DC motor of a motor driven surgical instrument, in accordance with the present invention.

Referring to FIG. 1, one preferred embodiment of a system 10 for controlling a motor driven surgical cutting instrument, in accordance with the present invention, is shown. System 10 includes a main control unit (MCU) 12, which is preferably a microprocessor-based system. MCU 12, as it relates to the present invention, is operable to control the various operations of the surgical cutting instrument handpiece 26 as well as manage the overall operation of system 10. A foot switch 14, which may be of known construction, is electrically connected to a number of inputs of MCU 12 via an equal number, K, of signal paths 16, wherein K may be any integer. As is known in the art, foot switch 14 is operated by the surgeon to provide MCU 12 with control signals to signal activation and deactivation of the cutting instrument handpiece 26 as well as to control the cutting speed thereof.

A control panel 18, which may be of known construction, is electrically connected to a number of inputs of MCU 12 via an equal number, J, of signal paths 20, wherein J may be any integer. Control panel 18 may include a number of control mechanisms for controlling various features the cutting instrument handpiece 26. Examples of such features may include, but are not limited to, the flow of irrigation fluid (not shown) provided to the handpiece 26, control of a vacuum source 42 connected to the handpiece 26, and the like.

A display unit 22, which may be of known construction, is electrically connected to a number of outputs of MCU 12 via an equal number, Q, of signal paths 24, wherein Q may be any integer. Display unit 22 preferably includes provisions for displaying various operational parameters of system 10 including, but not limited to, operational status of the cutting instrument handpiece 26, the speed of operation of the cutting tool 36, vacuum level, and the like.

A surgical cutting instrument 36 is disposed within a handpiece 26 and includes a brushed DC electrical motor 34 coupled to the cutting instrument or tool 36 via a motor drive shaft as will be described more fully hereinafter. The motor 34 is electrically connected to a motor control unit 28 via a number, M, of signal paths 30 wherein M may be any integer. The motor control unit 28 is, in turn, connected to a number of outputs of MCU 12 via an equal number, N, of signal paths 32. A motor shaft position sensor 38 is electrically connected to a motor shaft position feedback input (SPF) of MCU 12 via signal path 40, and provides a motor stop identification signal thereon as will be more fully described hereinafter. As it relates to the present invention, the motor shaft stop identification signal provided by sensor 38 on signal path 40 preferably provides MCU 12 with a motor stop identification signal as well as a cutter speed signal that is proportional to the motor speed for a geared system or identical to the motor speed for a direct drive system.

Handpiece 26 is further mechanically connected to a vacuum unit 42 via conduit 44, whereby the vacuum unit 42 provides a controllable vacuum level to handpiece 26 for suctioning excised tissue as is known in the art. Vacuum unit 42 is electrically connected to a vacuum control unit 46 via a number, P, of signal paths 48 wherein P may be any integer. The vacuum control unit 46 is, in turn, connected to a number of outputs of MCU 12 via an equal number, L, of signal paths 50, wherein L may be any integer. A vacuum sensor 52, which may be a temperature compensated solid-state pressure sensor, is preferably positioned within the conduit 44 and is electrically connected to a vacuum feedback (VF) input of MCU 12 via signal path 54. Alternatively, the vacuum sensor 52 may be disposed within handpiece 26 or within the vacuum unit 42 itself.

In operation, the MCU 12 is responsive to a vacuum command signal, preferably provided by a corresponding control mechanism associated with control panel 18 or equivalent control mechanism, to provide one or more corresponding vacuum control signals to vacuum control unit 46 along signal paths 50. The vacuum control unit 46, in turn, is responsive to the one or more vacuum control signals to activate the vacuum unit 42 to thereby provide handpiece 26 with a desired level of vacuum. The actual vacuum level provided to handpiece 26 is sensed by vacuum sensor 52 which provides a corresponding vacuum feedback signal to the vacuum feedback input VF of MCU 12. The MCU 12 is then operable to compare the vacuum feedback signal with the vacuum command signal and correspondingly adjust the one or more vacuum control signals to achieve the desired vacuum level within handpiece 26. Such closed-loop feedback techniques are well known in the control systems art.

In one alternative embodiment, the MCU 12 can be replaced by individual microprocessors controlling the input and output for controlling the operation of the motor driver 58 and the vacuum generator unit 42. In this alternative embodiment, the motor control and vacuum control microprocessors can be PIC16CXX Series microcontrollers provided by Microchip, Inc. of Chandler Ariz. The motor control microcontrollers can receive input signals from the motor driver 58 and position sensor 38, as well as the foot switch 14 and panel controls 18. Likewise, the vacuum microcontroller can receive input signals from the vacuum sensor 52, the foot switch and panel controls. Each microcontroller can provide its own output to its driven component and have its own display, such as an LED display, indicative of its operational status. Moreover, the two units can communicate with each other to ensure clean cutting by proper timing of the cutting and aspiration functions.

In one preferred embodiment, the handpiece 26 includes a control portion 62 having an elongated housing or cannula 64 extending therefrom. The cannula 64 terminates at a cannula tip 66 and defines an opening 68 near the tip 66. The cannula 64 is generally hollow and houses any of the various embodiments of the tissue cutting tool 36 as illustrated in FIGS. 4A, 5A, 6A and 7. In any case, cannula 64 is configured for insertion into a body site, and in one specific application of system 10 cannula 64 is configured to perform percutaneous ocular surgery. The connection of the vacuum unit 42 to cutting instrument handpiece 26 via conduit 44 is omitted in FIG. 2 for brevity and clarity of illustration of the brushed DC drive motor 34 and related components. It is to be understood, however, that such a vacuum connection is made to instrument handpiece 26 and is typically made between cannula 64 and control section 62. Moreover, although not specifically shown in the drawings, an irrigation fluid connection may also be made to cutting instrument handpiece 26 so that irrigation fluid may be passed to the surgical site via cannula opening 68.

Figure 2:
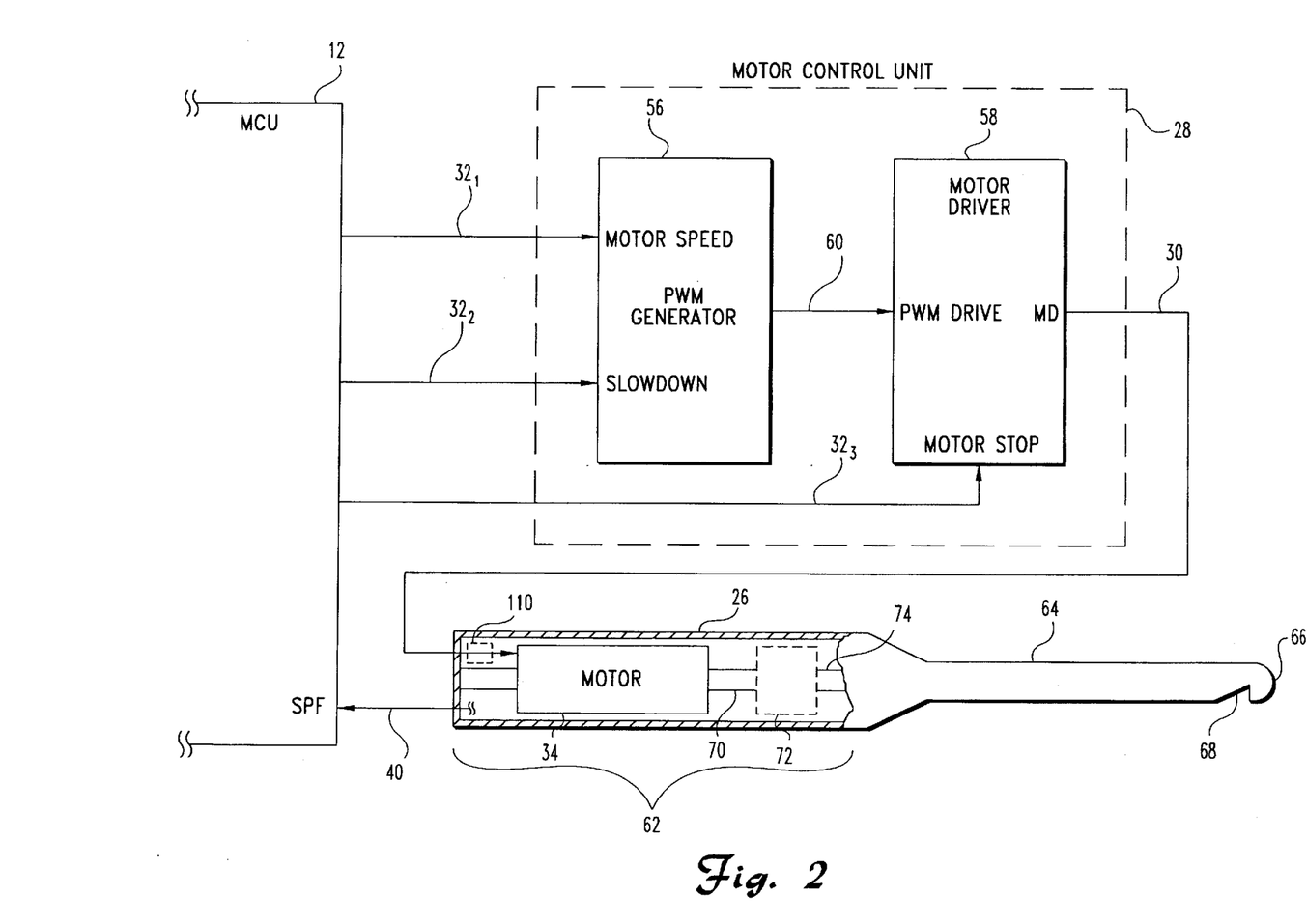
FIG. 2 is a diagrammatic illustration of the system of FIG. 1 showing further details of one embodiment of a motor control unit and the surgical instrument.
Figure 3A:
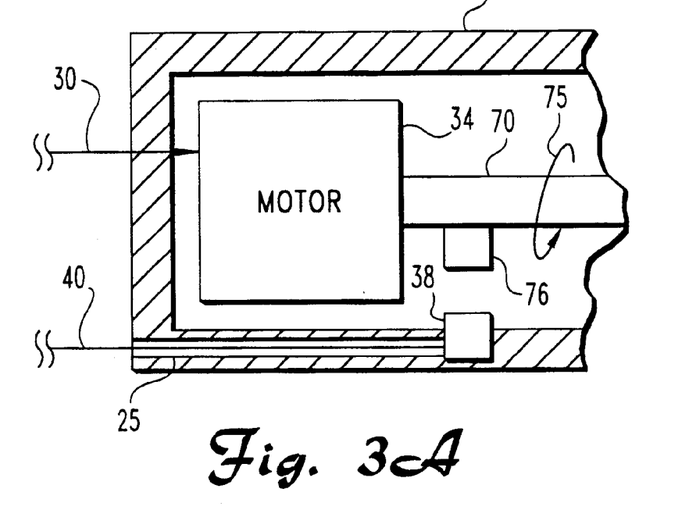
FIG. 3A is a cross sectional illustration of the handpiece of FIG. 2 showing details of a surgical instrument stop position identification mechanism for a rotationally driven motor shaft.
Figure 8:
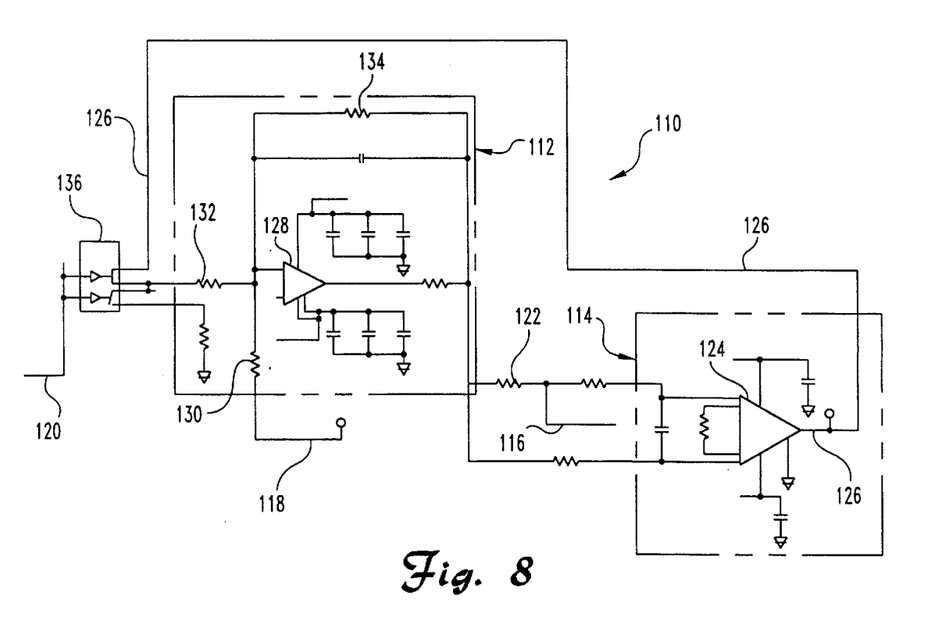
FIG. 8 is an electrical schematic of a motor control circuit for use with one embodiment of the invention.

Referring now to FIGS. 2 and 3A, preferred embodiments of the motor control unit 28 and handpiece 26 are shown in greater detail. The motor control unit 28 in one embodiment includes a pulse width modulation (PWM) generator circuit 56 having a motor speed input connected to one of the MCU outputs $32_1$. The output $32_1$ can provide a variable voltage signal indicative of a desired motor speed and based upon the position of a throttle or foot pedal. In certain embodiments, an additional input is connected to another one of the MCU outputs $32_2$. The signal at this output $32_2$ can be a motor slowdown signal as described below. Alternatively, the output $32_2$ can constitute a braking signal used in connection with a current feedback motor controller, as depicted in FIG. 8. As a further alternative, the slowdown command may be communicated via the motor speed command itself, rather than through a separate signal $32_2$. In this instance, the output $32_2$ may not be required.

In the illustrated embodiment, the PWM is disposed within the motor control unit. Alternatively, the PWM can be integrated into the MCU 12, or into the separate motor control microprocessor discussed above. The motor speed input receives a motor speed signal from MCU 12 indicative of desired operational speed of the drive motor 34. The slowdown input can receive a speed adjustment signal from the MCU 12 based on the actual motor speed signal provided by a motor sensor 76 associated with the drive motor 34, which motor sensor 76 will be described in greater detail hereinafter.

A motor driver circuit 58 is electrically connected to PWM generator circuit 56 via signal path 60 and receives a PWM drive signal therefrom, which is a pulse width modulated signal indicative of desired drive motor speed. The motor driver circuit 58 provides a motor drive signal (MD) to drive motor 34 via signal path 30. While the preferred embodiment contemplates digital control of the motor using the PWM generator circuit 56, alternative embodiments can utilize closed loop feedback analog circuits, particularly where slower cutting speeds are contemplated. One alternative controller is illustrated in FIG. 8 and described in more detail herein.

The motor drive signal includes a motor stop input that is connected to another one of the MCU outputs $32_3$. In accordance with the present invention, MCU provides a motor stop signal on signal path $32_3$, based on a motor deactivation command provided by foot switch 14 and also based on a motor stop identification signal provided by sensor 38, to stop the tissue cutting tool 36 in a desired position, as will be more fully described hereinafter. In certain embodiments, only the motor stop signal is utilized to command the motor to stop at the predetermined position. In these certain embodiments, the motor slowdown signal on path $32_2$ can be eliminated, or the input on path $32_2$ can be used for other control signals to the motor control circuit.

Drive motor 34 is preferably a known brushed DC electrical motor operable to drive a rotary motor shaft 70 connected thereto. In one embodiment of the present invention, the rotary motor shaft 70 is connected directly to a drive shaft 74 of a rotary cutting tool (see FIGS. 4A–4D and 5A–5D) disposed within the cannula 64 so that the cutting tool rotates about a longitudinal axis defined by the elongated cannula 64. In an alternative embodiment, the rotary motor shaft 70 is connected to one end of a transmission mechanism 72 which is operable to convert the rotary motion of the shaft 70 to a linearly reciprocating motion. The opposite end of the transmission mechanism 72 is connected to the drive shaft 74 of a linearly reciprocating cutting tool (see FIGS. 6A–6C, or 7) disposed within the cannula 64 so that the cutting tool reciprocates along the longitudinal axis of the cannula 64. An example of one known transmission mechanism for converting the rotary motion of shaft 70 to a linearly reciprocating motion is described in U.S. Pat. No. 5,411,513 to Ireland et al., the disclosure of which is incorporated herein by reference.

Figure 3B:
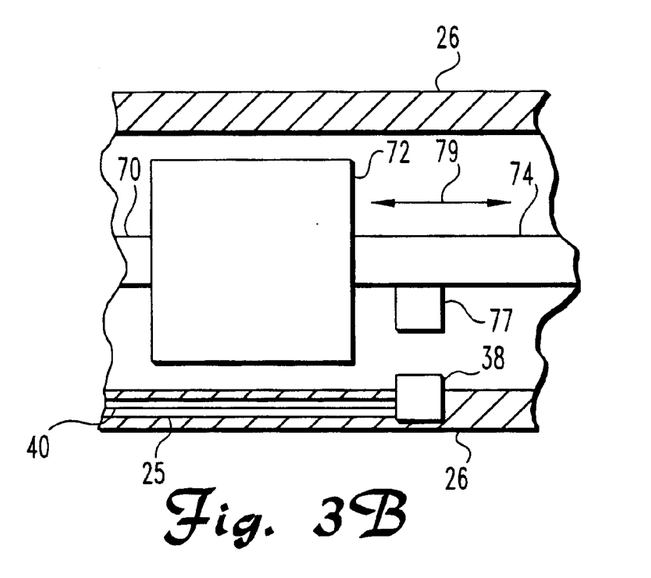
FIG. 3B is a cross sectional illustration of the handpiece of FIG. 2 showing details of a surgical instrument stop position identification mechanism for a linearly driven motor shaft.

Referring now to FIGS. 3A and 3B, preferred embodiments of a mechanism for determining the motor stop identification signal are shown. In the case that motor drive shaft 70 is connected directly to the drive shaft 74 of a rotary cutting instrument (FIGS. 4A and 5A), as shown in FIG. 3A, sensor 38 is preferably disposed within, or attached to, an inner surface of handpiece 26. A channel 25 is preferably formed within handpiece 26 and signal path 40 is disposed within channel 25 and electrically connected to sensor 38. In this manner, signal path 40 is isolated from the interior of handpiece 26. Shaft 70, shown in FIG. 3A as rotatably driven in the direction indicated by arrow 75, includes a shaft position identification mark 76 attached thereto or formed integral therewith. In the case that motor drive shaft 70 is connected to a transmission unit 72 which is then connected to the drive shaft 74 of a linearly reciprocating cutting instrument (see FIGS. 6A and 7), as shown in FIG. 3B, shaft 74 is linearly driven in the direction indicated by arrow 79 and includes a shaft position identification mark 77 attached thereto or formed integral therewith. Alternatively, mark 76 positioned on shaft 70 may be used even though handpiece 26 includes a transmission unit 72. In any case, sensor 38 is preferably a known Hall effect sensor, although the present invention contemplates utilizing other known sensors such as a variable reluctance sensor and the like. Marks 76 and 77 are preferably magnetized identifiers that align with sensor 38 when the cutting instrument is in a preferred stop position. Sensor 38 is operable to sense passage thereby of mark 76 or 77 and provide corresponding shaft speed and motor stop identification signals to input shaft position feedback input SPF of MCU 12 via signal path 40.

Figure 4A:
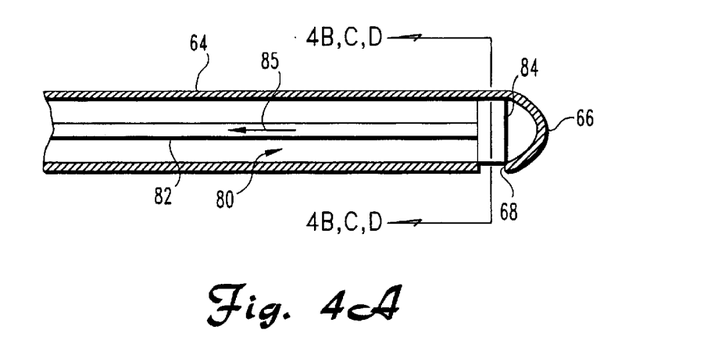
FIG. 4A is a cross sectional illustration of one embodiment of a rotary surgical cutting tool disposed within the cannula of the surgical instrument shown in FIG. 2.

Referring now to FIGS. 4A–4D, one embodiment 80 of the tissue cutting tool 36 of FIG. 1 in relation to the cannula 64 is shown. The rotary tissue cutting tool 80, as shown in FIG. 4A, preferably includes a shaft 82 connected to, or integral with, the rotary drive shaft 70 of FIG. 2. Since cutting tool 80 is configured for rotary motion within cannula 64, the transmission mechanism 72 is omitted and drive shafts 70 and 74 comprise a single drive shaft. Adjacent to the opening 68 formed near the tip 66 of cannula 64, the cutting tool 80 defines a number of blades or fins 84 that act as cutting surfaces. A vacuum is established within the cannula 64 via vacuum unit 42 (FIG. 1) so that a suction force is developed at the cannula opening 68 in the direction indicated by arrow 85.

Figure 4B:
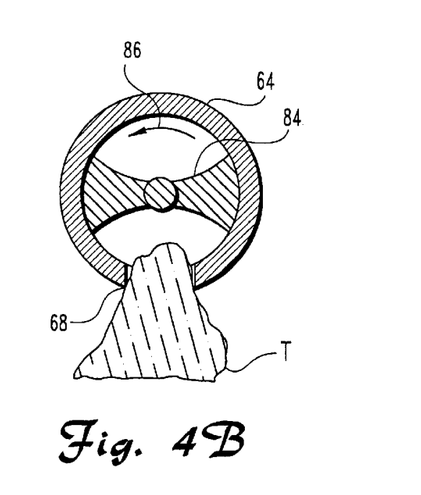
FIG. 4B is a cross sectional illustration of the surgical cutting tool of FIG. 4A, viewed along section lines 4B—4B, showing the cutting surfaces of the cutting tool positioned remote from the cannula opening.
Figure 4C:
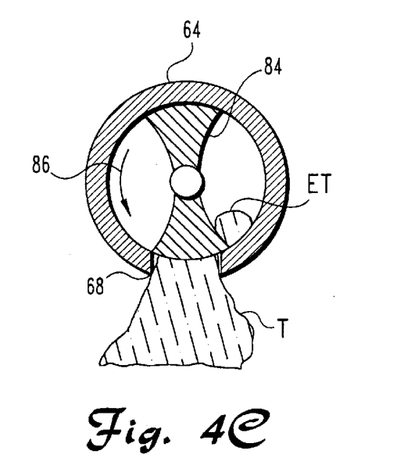
FIG. 4C is a cross sectional illustration of the surgical cutting tool of FIG. 4A, viewed along section lines 4C—4C, showing one of the cutting surfaces of the cutting tool excising a portion of the tissue forced into the opening near the cannula tip.

Referring to FIG. 4B, the drive motor 34 is activated pursuant to a motor activation command, typically provided via foot switch 14, wherein MCU 12 and motor control unit 28 are operable to process such a command as described hereinabove to cause motor 34 to rotate the one or more blades 84 in the direction indicated by arrow 86. The suction developed at the opening 68 of the cannula draws nearby tissue T into the opening 68 when the one or more blades 84 are disposed remote from the opening 68. As the one or more blades 84 rotate adjacent to the cannula opening 68, a portion of the excised tissue ET extending into opening 68 is excised as shown in FIG. 4C. The excised tissue ET is drawn away from opening 68 via vacuum and is collected by a suitable tissue container (not shown).

Figure 4D:
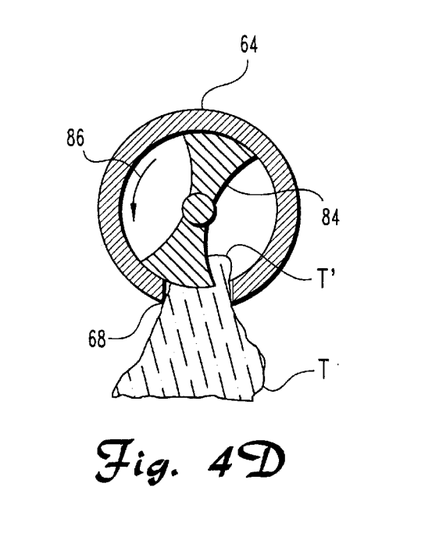
FIG. 4D is a cross sectional illustration of the surgical cutting tool of FIG. 4A, viewed along section lines 4D—4D, showing one of the cutting surfaces of the cutting tool trapping a portion of the tissue between the cutting tool and the opening near the tip of the cannula, which condition is avoided in accordance with the present invention.

The brushed DC drive motor 34 is deactivated, and the one or more blades 84 correspondingly cease to rotate, pursuant to a motor stop command provided by foot switch 14. However, unless the position of the rotary shaft 70, and hence the position of the one or more blades 84 relative to the cannula opening 68, is appropriately controlled when the motor 34 is deactivated, one of the blades 84 may come to rest partially disposed over opening 68 and consequently trap a portion of the tissue T' between the blade 84 and a boundary of the opening 68 as illustrated in FIG. 4D. Efforts at withdrawing the cannula 64 from the surgical site may accordingly result in tearing of the tissue portion T' away from the tissue base T. Heretofore, the surgeon encountering such tissue trapping would typically be required to re-activate the cutting tool 80 to release the tissue portion T' from its base T. In accordance with the present invention, however, such tissue trapping is avoided.

Figure 5A:
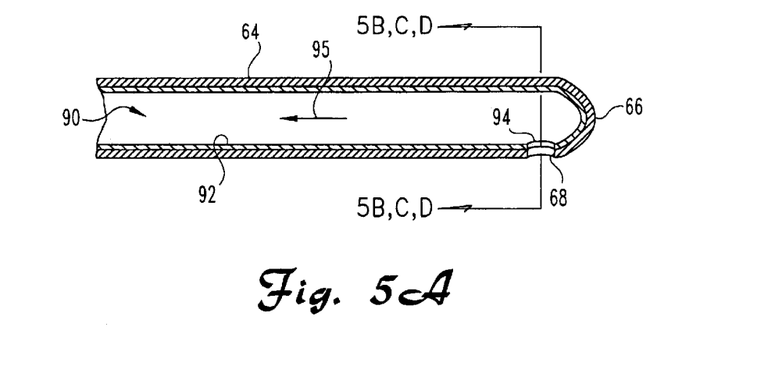
FIG. 5A is a cross sectional illustration of another embodiment of a rotary surgical cutting tool disposed within the cannula of the surgical instrument shown in FIG. 2.

Referring now to FIGS. 5A–5D, another embodiment 90 of the tissue cutting tool 36 of FIG. 1 in relation to the cannula 64 is shown. The rotary tissue cutting tool 90, as shown in FIG. 5A, preferably includes an elongated hollow tube 92 connected to, or integral with, the rotary drive shaft 70 of FIG. 2. Since cutting tool 90 is configured for rotary motion within cannula 64, the transmission mechanism 72 is omitted and drive shafts 70 and 74 comprise a single drive shaft. Adjacent to the opening 68 formed near the tip 66 of cannula 64, the cutting tool 90 defines an opening 94 defining a cutting surface at its boundary. Vacuum is established within the cannula 64 via vacuum unit 42 (FIG. 1) so that a suction force is developed at the cannula opening 68 in the direction indicated by arrow 95.

Figure 5B:
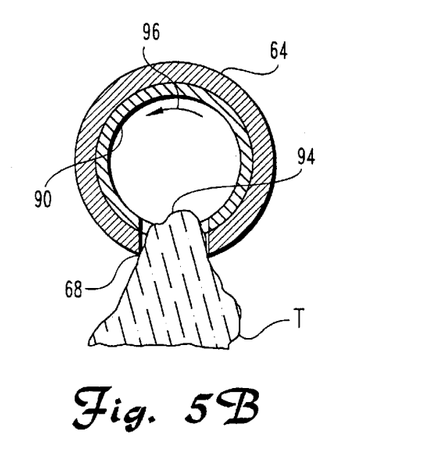
FIG. 5B is a cross sectional illustration of the surgical cutting tool of FIG. 5A, viewed along section lines 5B—5B, showing the cutting surface of the cutting tool positioned adjacent to the cannula opening.
Figure 5C:
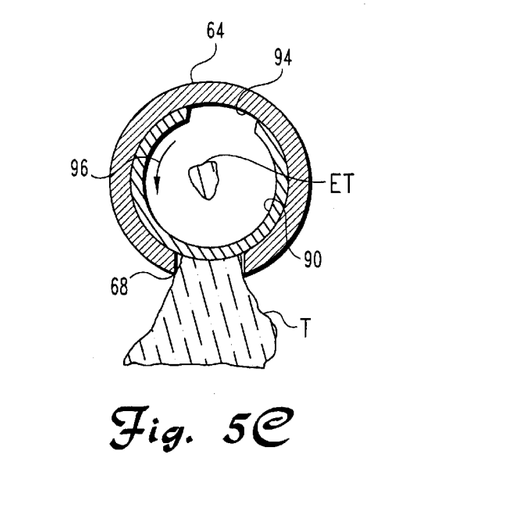
FIG. 5C is a cross sectional illustration of the surgical cutting tool of FIG. 5A, viewed along section lines 5C—5C, showing the cutting surface of the cutting tool disposed remote from the opening near the cannula tip after excising a portion of the tissue extending into the cannula opening.

Referring to FIG. 5B, the drive motor 34 is activated as described above to cause motor 34 to rotate the cutting opening 94 defined within cutting tool 90 in the direction indicated by arrow 96. The suction developed at the opening 68 of the cannula draws nearby tissue T into the opening 68 when the cutting tool opening 94 is aligned with the cannula opening 68. As the cutting tool opening 94 rotates away from the cannula opening 68, a portion of the tissue ET extending into openings 68 and 94 is excised as shown in FIG. 5C. The excised tissue ET is drawn away from opening 68 via vacuum and is collected by a suitable tissue container (not shown).

Figure 5D:
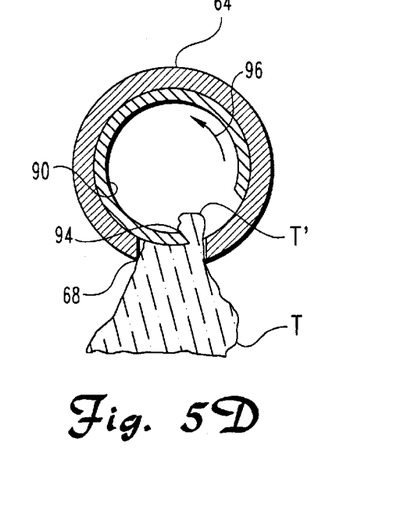
FIG. 5D is a cross sectional illustration of the surgical cutting tool of FIG. 5A, viewed along section lines 5D—5D, showing the cutting surface of the cutting tool trapping a portion of the tissue between the cutting tool and the opening near the tip of the cannula, which condition is avoided in accordance with the present invention.

As with the embodiment illustrated in FIGS. 4A–4D, the cutting tool opening 94 may come to rest partially disposed over opening 68 and consequently trap a portion of the tissue T' between a boundary of the cutting tool opening 94 and a boundary of the cannula opening 68, as illustrated in FIG. 5D, unless the position of the rotary shaft 70, and hence the position of the cutting tool opening 94 relative to the cannula opening 68, is appropriately controlled when the motor 34 is deactivated. Again, efforts at withdrawing the cannula 64 from the surgical site may accordingly result in tearing of the tissue portion T' away from the tissue base T, and a surgeon encountering such tissue trapping would typically be required to re-activate the cutting tool 90 to release the tissue portion T' from its base T.

Figure 6A:
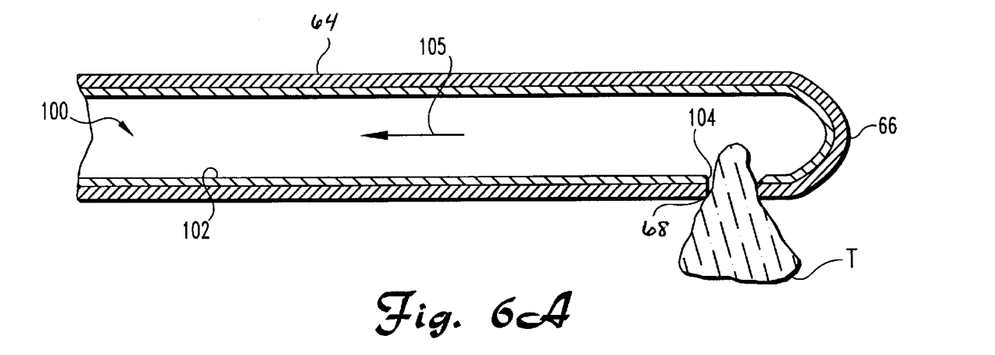
FIG. 6A is a cross sectional illustration of one embodiment of a linearly reciprocating surgical cutting tool disposed within the cannula of the surgical instrument shown in FIG. 2 showing the cutting surface of the cutting tool positioned adjacent to the cannula opening.
Figure 6B:
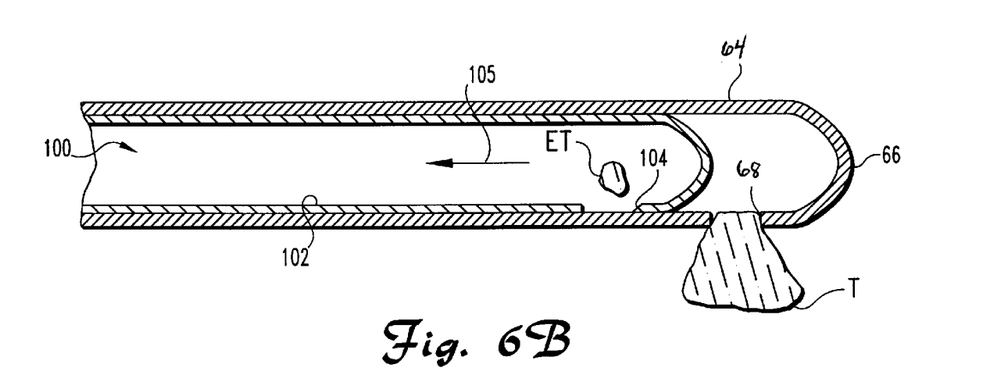
FIG. 6B is a cross sectional illustration of the surgical cutting tool of FIG. 6A showing the cutting surface of the cutting tool disposed remote from the opening near the cannula tip after excising a portion of the tissue extending into the cannula opening.
Figure 6C:
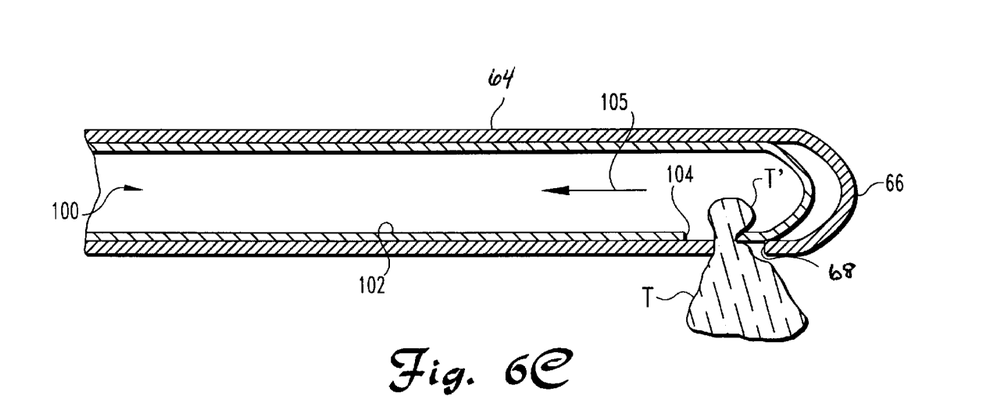
FIG. 6C is a cross sectional illustration of the surgical cutting tool of FIG. 6A showing the cutting surface of the cutting tool trapping a portion of the tissue between the cutting tool and the opening near the tip of the cannula, which condition is avoided in accordance with the present invention.

Referring now to FIGS. 6A–6C, yet another embodiment 100 of the tissue cutting tool 36 of FIG. 1 in relation to the cannula 64 is shown. The linearly reciprocating tissue cutting tool 100 preferably includes an elongated hollow tube 102 connected to, or integral with, the drive shaft 74 of FIG. 2. Since cutting tool 100 is configured for linearly reciprocating motion within cannula 64, the transmission mechanism 72 is operatively connected between drive shafts 70 and 74. Adjacent to the opening 68 formed near the tip 66 of cannula 64, the cutting tool 100 defines an opening 104 defining a cutting surface at its boundary. Vacuum is established within the cannula 64 via vacuum unit 42 (FIG. 1) so that a suction force is developed at the cannula opening 68 in the direction indicated by arrow 105.

The drive motor 34 operates as described to reciprocate the cutting opening 104 defined within cutting tool 100 linearly along the longitudinal axis of cannula 64. The suction developed at the opening 68 of the cannula draws nearby tissue T into the opening 68 when the cutting tool opening 104 is aligned with the cannula opening 68. As the cutting tool opening 104 pulls away from the cannula opening 68, a portion of the tissue ET extending into openings 68 and 104 is excised as shown in FIG. 5B. The excised tissue ET is drawn away from opening 68 via vacuum and is collected by a suitable tissue container (not shown).

As with the embodiments illustrated in FIGS. 4A–4D and 5A–5D, the cutting tool opening 104 may come to rest partially disposed over opening 68 and consequently trap a portion of the tissue T' between a boundary of the cutting tool opening 104 and a boundary of the cannula opening 68, as illustrated in FIG. 6C, unless the position of the rotary shaft 70, and hence the position of the cutting tool opening 104 relative to the cannula opening 68, is appropriately controlled when the motor 34 is deactivated. Again, efforts at withdrawing the cannula 64 from the surgical site may accordingly result in tearing of the tissue portion T' away from the tissue base T, and a surgeon encountering such tissue trapping would typically be required to re-activate the cutting tool 100 to release the tissue portion T' from its base T.

Figure 7:
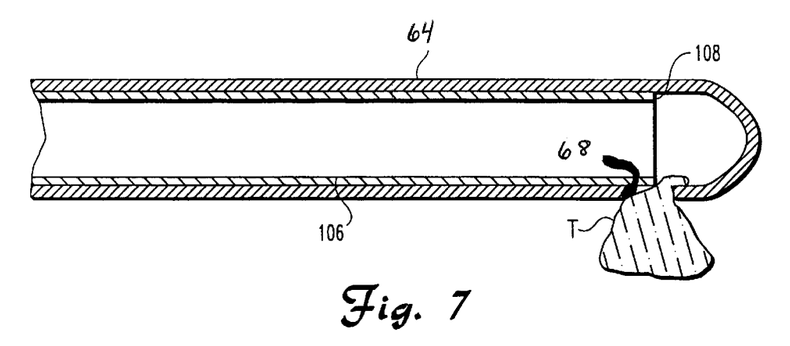
FIG. 7 is a cross sectional illustration of a further embodiment of a linearly reciprocating surgical cutting tool showing the cutting surface of the cutting tool trapping a portion of the tissue between the cutting tool and the opening near the tip of the cannula.

The reciprocating cutting instrument shown in FIGS. 6A–C can be modified to an end cutting configuration, such as depicted in FIG. 7. In this configuration, the cutting tool 106 is open at its distal end. The distal end defines a circumferential cutting surface 108 that excises the tissue T. As shown in FIG. 7, the cutting tool 106 can be stopped in a position in which a portion of the tissue is trapped between the cutting opening in the outer cannula 64 and the cutting surface 108, leading to the phenomena described above. The motor control system according to the illustrated embodiments of the present invention can adjust the stopped position of the cutting tool 106 so the end cutting surface 108 is clear of the cannula cutting opening.

In accordance with the present invention, the tissue trapping conditions illustrated in FIGS. 4D, 5D, 6C and 7 are avoided by controlling deactivation of the drive motor 34 in such a manner that the cutting surface(s) of the various cutting tools are positioned remote from the cannula opening 68. Referring again to FIGS. 2, 3A and 3B, controlled deactivation of the drive motor 34 will now be described in detail.

When it is desired to deactivate a presently activated cutting tool, such as any of the cutting tools illustrated in FIGS. 4A–4D, 5A–5D, 6A–6C or 7, a motor stop command is provided via foot switch 14 (FIG. 1). In one embodiment, MCU 12 is responsive to the motor stop command to provide a slowdown signal to the PWM generator via signal path $32_2$ which slows the action of motor 34. Preferably, the slowdown signal corresponds to a predefined signal level operable to drive the motor 34 at a motor speed below a motor speed threshold level. Since motor 34 is a brushed DC motor, it has a rotational resistance or resistive torque associated therewith as described above. In addition, in some cases friction between the inner and outer needles will increase the rotational resistance. Due to this combined rotational resistance, operation of the motor 34 will cease very rapidly or nearly instantly if the motor drive signal on signal path 30 is disabled while driving motor 34 below the motor speed threshold. Accordingly, alignment of mark 76 or 77 with sensor 38 preferably corresponds to a position of the cutting instrument at which there is no danger of trapping tissue between a cutting surface thereof and the cannula opening, and sensor 38 is operable to produce the motor stop identification signal when so aligned with mark 76 or 77. Alternatively, although mark 76 or 77 is preferably at the open position, it may be located at any known displacement from the open position, so long as sufficient delay is controllably introduced in the activation of the brake signal. This delay can compensate for the displacement of the alignment mark 76 or 77.

In one embodiment, MCU 12 is preferably operable to produce a motor stop signal on signal path $32_3$ when sensor 38 detects alignment of mark 76 or 77 therewith after one passage thereby of mark 76 or 77 since producing the slowdown signal on signal path $32_2$. Allowing one passage of mark 76 or 77 by sensor 38 after issuing the slowdown signal ensures that the drive speed of motor 34 is at or below the motor speed threshold when subsequently issuing the motor stop command, regardless of the position of mark 76 or 77 relative to sensor 38 when the slowdown command was issued. After one passage of mark 76 or 77 by sensor 38 since issuing the slowdown signal, MCU 12 is responsive to the signal provided by sensor 38 indicative of alignment of mark 76 or 77 therewith, to produce the motor stop signal on signal path $32_3$. The motor driver 58 is responsive to the motor stop signal to produce a motor disable signal on signal path 30. Due to the inherent rotational resistance, motor 34 is responsive to the motor disable signal to immediately cease operation thereof with mark 76 or 77 substantially aligned with sensor 38, and with the cutting instrument accordingly positioned so as not to trap tissue between any cutting surface thereof and the cannula opening. It is contemplated that the stopped position of the motor, and therefore the cutting surface, may be instead aligned with a predetermined differential distance between the mark 76/77 and the sensor 38. The braking characteristics of the cutter and its motor can be ascertained and the stopping distance determined so that this predetermined differential distance can be calibrated accordingly.

For example, with cutting tool 80, MCU 12 is preferably operable to stop the drive motor 34 as just described with the cutting blades 84 positioned as illustrated in FIG. 4B, although the present invention contemplates stopping the drive motor 34 with cutting blades 84 positioned otherwise relative to cannula opening 68 so long as tissue pinching does not occur as illustrated in FIG. 4D. With cutting tool 90, MCU 12 is preferably operable to stop the drive motor 34 as just described with the cutting opening 94 positioned as illustrated in FIG. 5C, although the present invention contemplates stopping the drive motor 34 with cutting opening 94 positioned otherwise relative to cannula opening 68 so long as tissue pinching does not occur as illustrated in FIG. 5D. Finally, with cutting tool 100, MCU 12 is preferably operable to stop the drive motor 34 as just described with the cutting opening 104 positioned as illustrated in FIG. 6B, although the present invention contemplates stopping the drive motor 34 with cutting opening 104 positioned otherwise relative to cannula opening 68 so long as tissue pinching does not occur as illustrated in FIG. 6C.

In some instances, the actual motor speed will be below the motor speed threshold when the motor stop command is issued by the surgeon. In these instances, the MCU can be programmed to recognize this condition and bypass the requirement of one passage of the mark 76 or 77 past the sensor. If the motor speed is already sufficiently slow, the MCU can simply disable the motor when the mark first encounters the sensor.

In a further modification, the motor disable signal can be provided to a relay spanning the motor terminals, such as relay 110 shown in phantom within the handpiece depicted in FIG. 2. Energizing the relay shorts across the terminals to immediately "kill" the motor. This motor short approach adds to the rotational resistance described above to ensure that the motor can be stopped repeatably and reliably. In addition, the shorting relay serves as a sort of fail-safe feature that prevents the possibility that motor can become re-energized while the cutting instrument is being removed from the patient. Alternatively, the motor slowdown signal can be eliminated, but the motor speed signal set to a speed of zero, which effectively results in shorting of the drive outputs. This action is equivalent to activating the relay 110, with the same improvements in stopping time.

In an alternative approach, the motor slowdown signal is eliminated. In this instance, the rotational resistance or natural braking characteristics of the motor and cutter can be quantified to determine how far the motor will rotate once current is terminated to the motor. Current can be supplied to the motor even after a motor stop signal has been received, until the motor control circuit receives a motor stop identification signal generated by the sensor 38. With the approach, the sensor 38 can be placed offset from the predetermined position at which cutting surface is clear of the cannula cutting opening. Thus, when the signal from sensor 38 is received, current to the motor can be terminated and the motor will coast to a stop at the appropriate position.

In the prior embodiment, the motor control circuit implements pulse width modulation to control the motor speed and operation. In a further embodiment, a control circuit shown in FIG. 8 relies upon current feedback to control the motor speed. Specifically, the control circuit 110 includes a current sensor 114 and a power amplifier circuit 112. The motor drive signal 116 is provided at the output of the power amplifier circuit 112. A speed control signal 118 is supplied as an input to the amplifier 112 circuit based upon a throttle position. The speed control signal 118 can be supplied at the signal path 32 (FIG. 1). Current to the motor drive signal 116 is delivered through the resistor 122. The output of the power amplifier circuit 112 is fed directly and through resistor 122 to a difference amplifier 124 in the current sensor 114. The output 126 of the difference amplifier is provided as a feedback signal to an input of the power amplifier circuit 112.

The amplifier circuit includes an op amp 128 that receives the feedback output 126 and the signal input 118 conditioned through a resistor 130. A resistor 134 scales and amplifies the input signals to supply the current signal to the motor drive signal 116.

In one aspect of the present embodiment, a feedback disable switch 136 is interposed between the feedback output 126 and the input to the power amplifier circuit 112. A braking signal 120 is supplied to the switch 136 to determine its state. In the illustrated position in FIG. 8, the switch 136 connects the feedback output 126 to the power amplifier circuit input. In its alternative position, the switch 136 connects the feedback output 126 to ground, thereby disabling the current feedback control feature of the drive circuit 110. In this instance, the absence of the current feedback increases the natural braking characteristics of the handpiece and drive motor.

The braking signal input 120 can be derived from the motor stop signal $32_3$ identified in FIG. 2. Alternatively, the braking signal input 120 can be connected to the output $32_2$, which had been used for a slowdown signal with the motor control circuit shown in FIG. 2. As with the prior embodiments, the motor control circuit 110 relies upon the natural rotational resistance and braking characteristics of the motor and cutter. These characteristics are particularly pronounced for a brushed DC motor and can be readily quantified.

While the invention has been illustrated and described in detail in the foregoing drawings and description, the same is to be considered as illustrative and not restrictive in character, it being understood that only the preferred embodiments have been shown and described and that all changes and modifications that come within the spirit of the invention are desired to be protected.

What is claimed is:

1. A tissue cutting apparatus comprising:

an elongated housing configured for insertion into a body site, said housing having a first end defining an opening adjacent thereto;

a tissue cutting tool disposed within said housing and defining at least one cutting surface configured for movement relative to said housing adjacent said opening to thereby excise tissue extending into said opening;

a motor driving a drive shaft extending therefrom and coupled to said cutting tool, said motor operable to drive said cutting tool at a cutting speed to excise tissue at said opening;

means for sensing a predefined position of said drive shaft relative to said housing and producing a stop position signal corresponding thereto, said predefined position corresponding to a position of said at least one cutting surface relative to said opening to avoid trapping unexcised tissue therebetween;

means for generating a motor stop signal when it is desired to stop said cutting tool; and a control circuit responsive to said motor stop signal to deactivate said motor with said drive shaft at a position prior to said predefined position so that said motor stops with said drive shaft substantially at said predefined position.

2. The tissue cutting apparatus of claim 1, wherein said motor is a brushed DC motor.

3. The tissue cutting apparatus of claim 1 wherein said motor is responsive to a motor activation signal provided by said control circuit to rotationally drive said drive shaft.

4. The tissue cutting apparatus of claim 3 wherein said drive shaft is connected to said cutting tool to thereby drive said cutting tool rotationally about a longitudinal axis defined by said elongated housing.

5. The tissue cutting apparatus of claim 3 further including transmission means disposed between said motor and said cutting tool for converting rotary motion from said rotating drive shaft to reciprocating linear motion of said cutting tool to thereby drive said cutting tool in a linearly reciprocating fashion relative to a longitudinal axis defined by said elongated housing.

6. The tissue cutting apparatus of claim 3 wherein said means for sensing a predefined position of said drive shaft relative to said housing includes:
a mark associated with said drive shaft; and
a sensor operable to sense passage thereby of said mark and produce said stop position signal.

7. The tissue cutting apparatus of claim 6 wherein said mark is a magnetized identifier attached to said drive shaft.

8. The tissue cutting apparatus of claim 7, wherein said sensor is a Hall effect sensor attached to said housing.

9. The tissue cutting apparatus of claim 3 wherein:
said motor activation signal is a variable motor speed signal; and
further including a motor control circuit disposed between said control circuit and said motor, said motor control circuit responsive to said variable motor speed signal to drive said motor at a corresponding rotational speed.

10. The tissue cutting apparatus of claim 9 wherein said motor control circuit includes:
a pulse width modulation (PWM) signal generator responsive to said motor speed signal to produce a corresponding PWM signal; and
a motor driver circuit responsive to said PWM signal to drive said motor at a corresponding rotational speed.

11. The tissue cutting apparatus of claim 1 further including a vacuum unit coupled to said housing for creating a vacuum therein.

12. The tissue cutting apparatus of claim 11 further including a vacuum control circuit disposed between said control circuit and said vacuum unit, said vacuum control circuit responsive to at least one vacuum control signal provided by said control circuit to control said vacuum unit.

13. The tissue cutting apparatus of claim 1, wherein:
said motor includes motor terminals for receiving signals from said control circuit; and
said control circuit includes a relay spanning said motor terminals and operable in response to said motor stop signal to cause a short circuit across said terminals.

14. A tissue cutting apparatus comprising:
an elongated housing configured for insertion into a body site, said housing having a first end defining an opening adjacent thereto;
a tissue cutting tool disposed within said housing and defining at least one cutting surface configured for movement relative to said housing adjacent said opening to thereby excise tissue extending into said opening;
a motor driving a drive shaft extending therefrom and coupled to said cutting tool, said motor operable to drive said cutting tool at a cutting speed to excise tissue at said opening;
a control circuit operable to generate a motor activation signal, wherein said motor activation signal is a variable motor speed signal; and
a motor control circuit disposed between said control circuit and said motor, said motor control circuit responsive to said variable motor speed signal to drive said motor at a corresponding rotational speed,
wherein said motor control circuit includes:
a power amplifier providing a current signal to said motor; and
a current sensor sensing the current provided to said motor and providing a current feedback to said power amplifier, whereby said power amplifier is responsive to said current feedback to control the current signal provided to said motor.

15. The tissue cutting apparatus of claim 14, wherein said motor control circuit includes a switch disposed between said current sensor and said power amplifier operable to disable said current feedback in response to said motor stop signal.

16. A tissue cutting apparatus comprising:
an elongated housing configured for insertion into a body site, said housing having a first end defining an opening adjacent thereto;
a tissue cutting tool disposed within said housing and defining at least one cutting surface configured for movement relative to said housing adjacent said opening to thereby excise tissue extending into said opening;
a motor driving a drive shaft extending therefrom and coupled to said cutting tool, said motor operable to drive said cutting tool at a cutting speed to excise tissue at said opening;
means for sensing a predefined position of said drive shaft relative to said housing and producing a stop position signal corresponding thereto, said predefined position corresponding to a position of said at least one cutting surface relative to said opening to avoid trapping unexcised tissue therebetween;
means for generating a motor stop signal when it is desired to stop the cutting apparatus; and
a control circuit responsive to said motor stop signal to drive said motor at a predefined motor speed substantially less than said cutting speed and thereafter responsive to said stop position signal to deactivate said motor with said drive shaft at said predefined position.

17. The tissue cutting apparatus of claim 16, wherein said motor is a brushed DC motor.

18. A tissue cutting apparatus comprising:
an elongated housing configured for insertion into a body site, said housing defining a cutting opening sized to receive tissue therethrough;
a cutting member operatively disposed within said housing and defining a cutting surface adjacent said cutting opening configured to excise tissue projecting through said opening;
a brushed DC motor having a rotating output shaft coupled to said cutting member and operable to drive said cutting member at a cutting speed sufficient to excise tissue, said brushed DC motor generating a resistance torque in a direction opposite to the direction of rotation of said output shaft;
a position identifier mark associated with either of said output shaft or said cutting member;

a position sensor mounted in said housing in alignment with said position identifier mark, said sensor having a predetermined position relative to said cutting opening so that when said position identifier mark is immediately adjacent said position sensor, said cutting surface is disposed relative to said opening so that tissue projecting through said cutting opening is not trapped by said cutting surface; and means for generating a stop signal when it is desired to stop operation of said cutting member; and a motor controller providing power to said brushed DC motor and having means for controlling the operation of said motor, said means operable in a first state to control said motor at said cutting speed, in a second state to control said motor at a reduced speed sufficient only to overcome said resistive torque in response to said stop signal, and a third state to terminate power to said motor immediately after the second passage of said position identifier mark by said position sensor.

19. The tissue cutting apparatus according to claim 18, wherein said motor controller includes:

a power amplifier providing a current signal to said motor;

a current sensor sensing the current provided to said motor and providing a current feedback to said power amplifier, whereby said power amplifier is responsive to said current feedback to control the current signal provided to said motor; and a switch disposed between said current sensor and said power amplifier operable to disable said current feedback to said power amplifier in response to said stop signal.

20. The tissue cutting apparatus of claim 19, wherein:

said motor includes motor terminals for receiving signals from said control circuit; and said motor controller includes a relay spanning said motor terminals and operable in response to said stop signal to cause a short circuit across said terminals.

* * * * *